(12) United States Patent
Allen, IV et al.

(10) Patent No.: US 8,756,785 B2
(45) Date of Patent: Jun. 24, 2014

(54) SURGICAL INSTRUMENT SHAFTS AND METHODS OF MANUFACTURING SHAFTS FOR SURGICAL INSTRUMENTS

(75) Inventors: James D. Allen, IV, Broomfield, CO (US); Kim V. Brandt, Loveland, CO (US); Monte S. Fry, Longmont, CO (US); Keir Hart, Lafayette, CO (US); Daniel A. Joseph, Golden, CO (US); Peter M. Mueller, Frederick, CO (US); Jeffrey R. Unger, Longmont, CO (US)

(73) Assignee: Covidien LP, Mansfield, MA (US)

( * ) Notice: Subject to any disclaimer, the term of this patent is extended or adjusted under 35 U.S.C. 154(b) by 440 days.

(21) Appl. No.: 13/248,976

(22) Filed: Sep. 29, 2011

(65) Prior Publication Data

US 2013/0082035 A1 Apr. 4, 2013

(51) Int. Cl.
*B23K 20/12* (2006.01)
*B23K 26/20* (2014.01)
*B23P 11/00* (2006.01)
*B21D 35/00* (2006.01)

(52) U.S. Cl.
CPC .................. *B23P 11/00* (2013.01); *B23K 26/20* (2013.01); *B23K 20/12* (2013.01); *B21D 35/002* (2013.01)
USPC ............ 29/428; 29/469; 228/112.1; 228/177; 228/182; 219/121.64

(58) Field of Classification Search
CPC ........ B23K 20/12; B23K 26/20; B23P 11/00; B21D 35/00; B21D 35/002
USPC ......... 29/428, 469; 228/112.1, 177, 178, 182, 228/189; 219/121.64
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Samuel M Heinrich

(57) ABSTRACT

A method of manufacturing a shaft of a surgical instrument including forming a proximal segment of the shaft to include one or more features for operably engaging the shaft to a first component of the surgical instrument, forming a distal segment of the shaft to include one or more features for operably engaging the shaft to a second component of the surgical instrument and forming an intermediate segment of the shaft. The proximal segment is welded to a proximal end of the intermediate segment; and the distal segment is welded to a distal end of the intermediate segment. The proximal and distal segments are welded to the intermediate segment such that the one or more features thereof are aligned in a predetermined orientation relative to one another.

19 Claims, 3 Drawing Sheets

(56) References Cited

U.S. PATENT DOCUMENTS

| | | | |
|---|---|---|---|
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| 5,762,069 A * | 6/1998 | Kelleher et al. | 600/564 |
| H1745 H | 8/1998 | Paraschac | |
| 5,810,876 A * | 9/1998 | Kelleher | 606/205 |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| 6,403,916 B1 * | 6/2002 | Spooner et al. | 219/121.63 |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 19946527 | 12/2001 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2003-245285 | 9/2003 |
| JP | 2004-517668 | 6/2004 |
| JP | 2004-528869 | 9/2004 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 05/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Homer.
U.S. Appl. No. 13/072,945, filed Mar. 28, 2011, Patrick L. Dumbauld.
U.S. Appl. No. 13/080,383, filed Apr. 5, 2011, David M. Garrison.

(56) References Cited

OTHER PUBLICATIONS

U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Homer.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012 Kim V. Brandt.
U.S. Appl. No. 13/404,476, filed Feb. 24, 2012, Kim V. Brandt.

Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.

(56) References Cited

OTHER PUBLICATIONS

Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Intl Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.

(56) References Cited

OTHER PUBLICATIONS

Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/USO4/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

\* cited by examiner

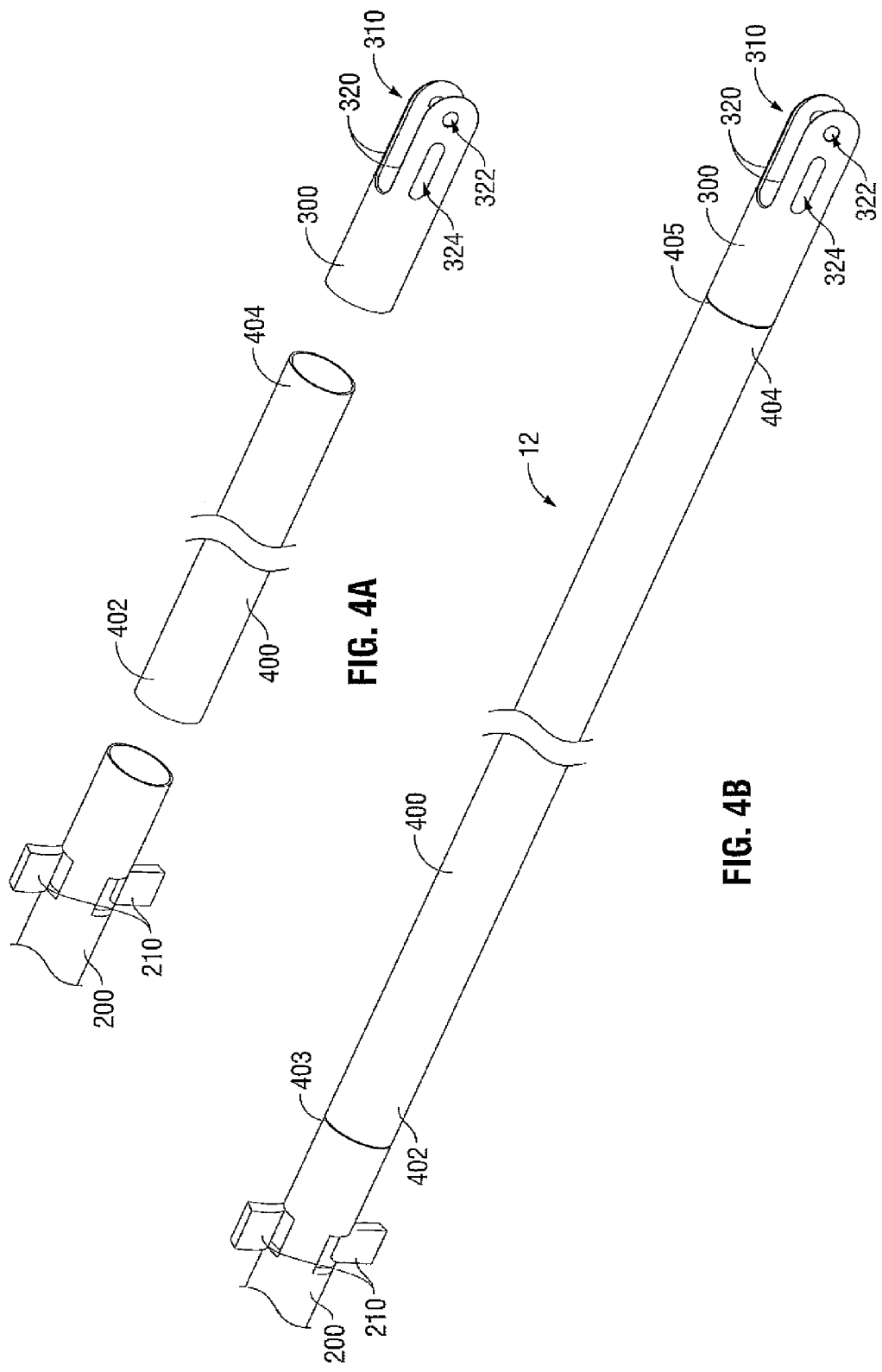

SURGICAL INSTRUMENT SHAFTS AND METHODS OF MANUFACTURING SHAFTS FOR SURGICAL INSTRUMENTS

BACKGROUND

The present disclosure relates to surgical instruments and, more particularly, to surgical forceps for grasping, sealing, and/or dividing tissue.

TECHNICAL FIELD

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many vessel sealing instruments have been designed which incorporate a knife or blade member that effectively severs the tissue after forming a tissue seal.

An endoscopic surgical forceps typically includes an elongated shaft having an end effector assembly, e.g., a pair of jaw members, disposed at the distal end thereof. The elongated shaft permits the surgeon to insert the end effector assembly through a relatively small access opening in the body to the internal surgical site, while the housing of the endoscopic forceps remains disposed externally of the surgical site. The surgeon may then control the operation of the end effector assembly, e.g., to grasp, seal, and/or divide tissue, by manipulating the housing.

As can be appreciated, the shafts of surgical instruments typically include numerous mechanical features at the ends thereof to facilitate operative engagement of the end effector assembly to the shaft at one end thereof and the housing, or handle assembly at the other end thereof such that the surgeon may operate the end effector assembly by manipulating mechanical components coupled to the housing.

SUMMARY

As used herein, the term "distal" refers to the portion that is being described which is further from a user, while the term "proximal" refers to the portion that is being described which is closer to a user.

Any or all of the aspects described herein, to the extent they are consistent, may be used in conjunction with any of the other aspects described herein.

A method of manufacturing a shaft of a surgical instrument is provided in accordance with the present disclosure. The method includes forming a proximal segment of the shaft to include one or more features for operably engaging the shaft to a first component of the surgical instrument, forming a distal segment of the shaft to include one or more features for operably engaging the shaft to a second component of the surgical instrument, and forming an intermediate segment of the shaft. The proximal segment of the shaft is welded to a proximal end of the intermediate segment and the distal end of the shaft is welded to a distal end of the intermediate segment. The welding of the proximal segment and/or the distal segment to the intermediate segment is configured such that the feature(s) of each of the proximal and distal segments are aligned in a pre-determined orientation relative to one another.

In one aspect, the proximal segment and/or the distal segment are welded to the intermediate segment via laser welding. Alternatively, the proximal segment and/or the distal segment may be welded to the intermediate segment via spin-welding, or one of the proximal and distal segments may be welded via laser welding, while the other is welded via spin-welding.

In another aspect, the welding of the proximal segment and the welding of the distal segment to the proximal and distal ends of the intermediate segment, respectively, are performed simultaneously and are clocked to one another to ensure alignment of the proximal segment and the distal segment in the pre-determined orientation relative to one another.

In yet another aspect, the intermediate segment is formed via tube-drawing. Further, the formed intermediate segment may be cut to a pre-determined length prior to welding of the proximal and distal segments thereto.

Another method of manufacturing a shaft of a surgical instrument is also provided in accordance with the present disclosure. The method includes forming a proximal segment of the shaft, forming a distal segment of the shaft, forming an intermediate segment of the shaft, and spin-welding the proximal segment of the shaft to a proximal end of the intermediate segment and the distal segment of the shaft to a distal end of the intermediate segment. The proximal and distal segments are clocked to one another during spin-welding to ensure alignment of the proximal and distal segments in a pre-determined orientation relative to one another.

In one aspect, the proximal segment and/or the distal segment are formed to include one or more features for operably engaging the shaft to the surgical instrument. The proximal and distal segments may be clocked to one another during spin-welding to ensure proper alignment of the feature(s) of each of the proximal and distal segments in the pre-determined orientation relative to one another.

In another aspect, the proximal and distal segments are simultaneously spin-welded to the intermediate segment.

In yet another aspect, the proximal segment and/or the distal segment are formed via stamping. The intermediate segment, on the other hand, may be formed via tube-drawing and/or may be cut to a pre-determined length prior to welding of the proximal and distal segments thereto.

In accordance with the present disclosure, another method of manufacturing a shaft of a surgical instrument is provided. The method includes stamping a proximal segment of the shaft to include one or more features for operably engaging the shaft to a first component of the surgical instrument, stamping a distal segment of the shaft to include one or more features for operably engaging the shaft to a second component of the surgical instrument, forming an intermediate segment of the shaft, cutting the intermediate segment to a pre-determined length, welding the proximal segment of the shaft to a proximal end of the intermediate segment, and welding the distal segment of the shaft to a distal end of the intermediate segment.

The proximal segment and the distal segment may be welded to the intermediate segment via laser welding, spin-welding, or any other suitable welding method. The intermediate segment, on the other hand, may be formed via tube-drawing.

In another aspect, welding of the proximal segment and/or the distal segment to the intermediate segment is configured such that the feature(s) of each of the proximal and distal segments are aligned in a pre-determined orientation relative to one another.

BRIEF DESCRIPTION OF THE DRAWINGS

Various aspects of the present disclosure are described herein with reference to the drawings wherein like reference numerals identify similar or identical elements:

FIG. 4A is a side view of the shaft of the forceps of FIG. 1 shown with parts separated; and FIG. 4B is a side view of the shaft of the forceps of FIG. 1 in an assembled condition.

DETAILED DESCRIPTION

Figure 1:
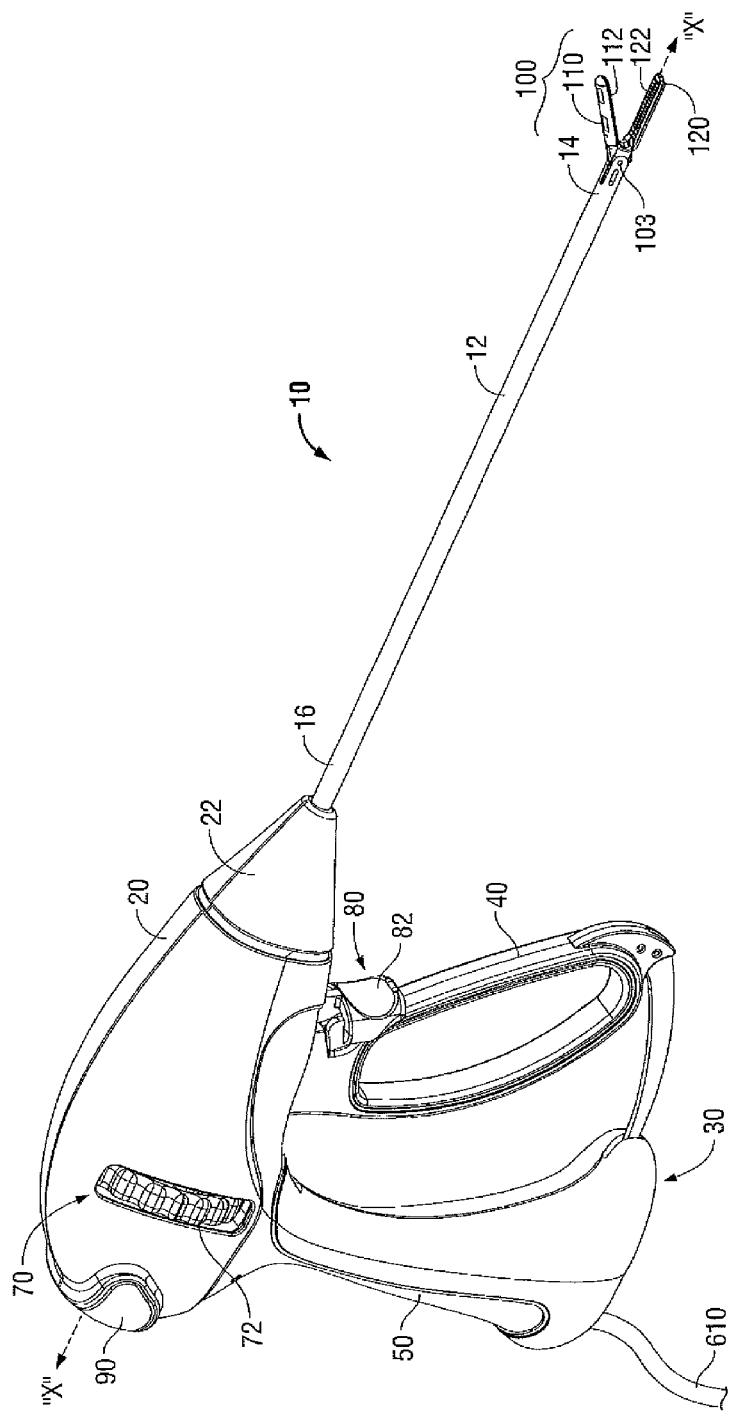
FIG. 1 is a front, perspective view of a surgical forceps provided in accordance with the present disclosure.

Referring now to FIG. 1, a forceps 10 configured for use in connection with endoscopic surgical procedures is shown. Forceps 10 is one example of a shaft-based surgical instrument incorporating the features of the present disclosure. As can be appreciated, the presently disclosed features detailed below are equally applicable to other shaft-based surgical instruments and are described with reference to forceps 10 for exemplary purposes only. Obviously, different electrical and mechanical connections and considerations may apply to each particular type of instrument; however, the novel aspects of the present disclosure remain generally consistent with respect to most shaft-based surgical instruments.

With continued reference to FIG. 1, forceps 10 defines a longitudinal axis "X-X" and includes a housing 20, a handle assembly 30, a rotating assembly 70, a trigger assembly 80 and an end effector assembly 100. Forceps 10 further includes a shaft 12 having a distal end 14 configured to mechanically engage end effector assembly 100 and a proximal end 16 that extends into housing 20 and is mechanically engaged to distal cone 22 of housing 20 (see FIG. 2). Forceps 10 also includes electrosurgical cable 610 that connects forceps 10 to a generator (not shown) or other suitable power source, although forceps 10 may alternatively be configured as a battery powered instrument. Cable 610 includes a wire (or wires) (not shown) extending therethrough that has sufficient length to extend through shaft 12 in order to provide electrical energy to the end effector assembly 100, e.g., upon activation of activation switch 90.

Continuing with reference to FIG. 1, handle assembly 30 includes fixed handle 50 and a moveable handle 40. Fixed handle 50 is integrally associated with housing 20 and handle 40 is moveable relative to fixed handle 50. Rotating assembly 70 includes a rotatable wheel 72 that is rotatable in either direction about longitudinal axis "X-X" to rotate end effector assembly 100 about longitudinal axis "X-X." Housing 20 houses the internal working components of forceps 10.

End effector assembly 100 is shown attached at a distal end 14 of shaft 12 and includes a pair of opposing jaw members 110 and 120. Each of the jaw members 110 and 120 includes an opposed electrically conductive tissue-sealing plate 112, 122, respectively. End effector assembly 100 is designed as a unilateral assembly, i.e., where jaw member 120 is fixed relative to shaft 12 and jaw member 110 is moveable about pivot 103 relative to shaft 12 and fixed jaw member 120. However, end effector assembly 100 may alternatively be configured as a bilateral assembly, i.e., where both jaw member 110 and jaw member 120 are moveable about pivot 103 relative to one another and to shaft 12. In some embodiments, a knife assembly (not shown) is disposed within shaft 12 and a knife channel 125 (FIG. 3) is defined within one or both of the jaw members 110, 120, to permit reciprocation of a knife blade (not shown) therethrough, e.g., via activation of a trigger 82 of trigger assembly 80.

Referring still to FIG. 1, moveable handle 40 of handle assembly 30 is ultimately connected to a drive assembly (not shown) that, together, mechanically cooperate to impart movement of jaw members 110 and 120 between a spaced-apart position and an approximated position to grasp tissue disposed between sealing plates 112 and 122 of jaw members 110, 120, respectively. As shown in FIG. 1, moveable handle 40 is initially spaced-apart from fixed handle 50 and, correspondingly, jaw members 110, 120 are disposed in the spaced-apart position. Moveable handle 40 is actuatable from this initial position to a depressed position corresponding to the approximated position of jaw members 110, 120.

With reference to FIGS. 2-4B, shaft 12 of forceps 10 is shown. Shaft 12 defines a generally cylindrically-shaped configuration, although other configurations are contemplated, and may be formed from any suitable biocompatible material. More particularly, shaft 12 is formed from three different segments: a proximal segment 200, a distal segment 300, and an elongated intermediate segment 400 that extends between and couples the proximal and distal segments 200, 300, respectively, to one another. However, greater or fewer than three segments may be provided, depending on the configuration of the particular surgical instrument incorporating shaft 12. In other words, although shaft 12 is shown including specifically-configured proximal and distal segments 200, 300, respectively, for engagement with housing 20 and end effector assembly 100, respectively, of forceps 10 (FIG. 1), shaft 12 may include various different segments of different configurations adapted to secure shaft 12 to the end effector assembly and housing, or handle assembly of any other suitable surgical instrument. As such, the particular features of proximal and distal segments 200, 300, respectively, detailed below are only exemplary.

Figure 2:
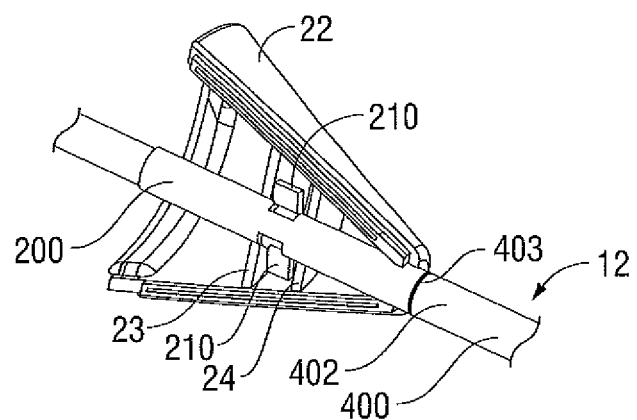
FIG. 2 is a longitudinal, cross-sectional view of the shaft of the forceps of FIG. 1 shown coupled to a housing of the forceps of FIG. 1 at a proximal end thereof.

Proximal segment 200 of shaft 12, as best shown in FIG. 2, extends proximally from proximal end 402 of intermediate segment 400 (FIGS. 4A-4B) into distal cone 22 of housing 20 (FIG. 1). More specifically, proximal segment 200 of shaft 12 extends through first and second retaining discs 23, 24, respectively, disposed within distal cone 22 of housing 20 (FIG. 1). Proximal segment 200 further includes a pair of tabs 210 extending radially-outwardly therefrom that are disposed between first and second retaining discs 23, 24, respectively, to engage shaft 12 within distal cone 22 of housing 20 (FIG. 1) in fixed longitudinal relation therewith, while still permitting shaft 12 to be rotated about longitudinal axis "X-X" relative to housing 20 (FIG. 1), e.g., via rotation of wheel 72 of rotating assembly 70 (FIG. 1). Proximal segment 200 and tabs 210 extending therefrom may be monolithically formed as a single component, e.g., via stamping. Stamping is a relatively inexpensive process and is advantageous in that specific features, e.g., tabs 210, mounting flanges 320 (FIG. 3-4B), apertures 322 (FIG. 3-4B), cam slots 324 (FIG. 3-4B), etc., may be subsequently or simultaneously formed through the stamped components, as desired.

Figure 3:
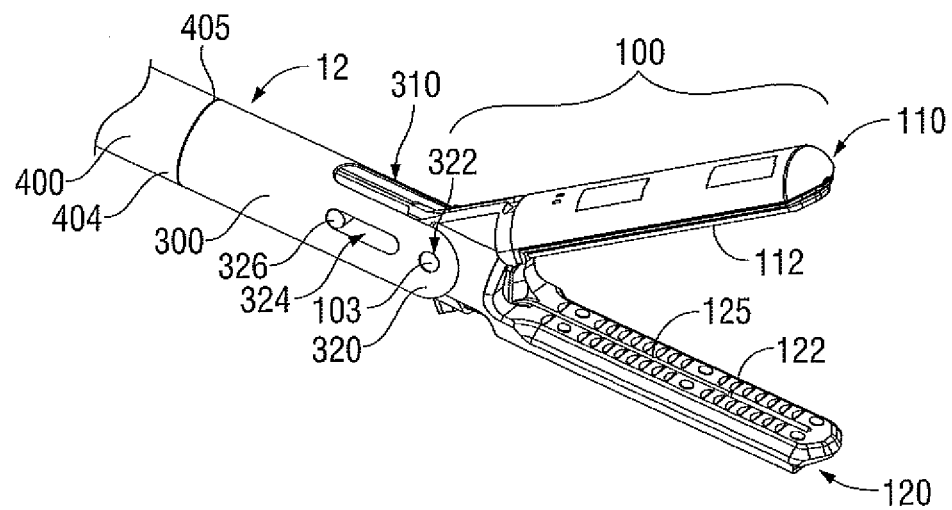
FIG. 3 is an enlarged, side perspective view of an end effector assembly coupled to a distal end of a shaft of the forceps of FIG. 1.

Distal segment 300 of shaft 12, as best shown in FIG. 3, extends distally from distal end 404 of intermediate segment 400 (FIGS. 4A-4B) and includes a clevis 310. Clevis 310 of distal segment 300 includes a pair of mounting flanges 320 that are formed with distal segment 300 of shaft 12 and extend therefrom in spaced-relation relative to one another. Each of the mounting flanges 320 includes an aperture 322 defined therethrough that is configured to receive pivot pin 103 (FIG. 1) therethrough to pivotably mount jaw members 110, 120 between mounting flanges 320. More specifically, mounting flanges 320 are configured to be positioned on either side of jaw members 110, 120 such that pivot pin 103 may inserted through aperture 322 of one of mounting flanges 320, through apertures (not explicitly shown) defined within each of jaw members 110, 120, and through aperture 322 defined within the other mounting flange 320 to pivotably engage jaw members 110, 120 of end effector assembly 100 to mounting flanges 320 of clevis 310 of distal segment 300 of shaft 12.

In embodiments where end effector assembly 100 is designed as a unilateral assembly, e.g., as shown in FIGS. 1 and 3, jaw member 120 may be fixedly engaged to one or both of mounting flanges 320, while jaw member 110 is pivotably moveable relative thereto between the spaced-apart and approximated positions. On the other hand, in bilateral embodiments, both of jaw members 110, 120 are pivotably coupled to mounting flanges 320.

Mounting flanges 320 of clevis 310 of distal segment 300 of shaft 12 each further include a cam slot 324 defined therethrough. Cam slots 324 are configured to receive drive pin 326 therethrough. Drive pin 326 extends from the drive bar (not shown) of the drive assembly (not shown) and is disposed within cam slots 324 of mounting flanges 324 as well as a cam slot (not shown) defined within jaw member 110 (and/or jaw member 120). The drive bar (not shown) of the drive assembly (not shown), is selectively translatable through shaft 12 and relative to end effector assembly 100 e.g., upon actuation of moveable handle 40 of handle assembly 30, to translate drive pin 326 along cam slots 324 and along the cam slot (not shown) defined within jaw member 110 (and/or jaw member 120) to urge jaw member 110 to pivot about pivot pin 103 relative to jaw member 120 between the spaced-apart position and the approximated position to grasp tissue therebetween. Distal segment 300 of shaft 12, including mounting flanges 320 of clevis 310, and apertures 322 and cam slots 324 thereof, may be monolithically formed as a single component via stamping or any other suitable process.

Intermediate segment 400 of shaft 12, as best shown in FIGS. 4A-4B, defines a cylindrically-shaped configuration and has a length sufficient for insertion of end effector assembly 100 of forceps 10 into an internal surgical site, while housing 20 of forceps 10 remains disposed externally of the surgical site. Intermediate segment 400 may be a drawn tube cut to a pre-determined length, or may be formed via any other suitable process. More specifically, since intermediate segment 400 is simply a cylindrical tube and does not include any of the complex features of proximal segment 200, e.g., tabs 210, or distal segment 300, e.g., clevis 310 and the components and features thereof, intermediate segment 400 may be formed, for example, by tube-drawing and may then be cut to a pre-determined length, i.e., a desired length. Tube-drawing is advantageous in that it is a relatively inexpensive, simple, and precise method of forming a shaft with a smooth surface finish and precise, consistent dimensions. Such features facilitate the insertion of shaft 12 into and the removal of shaft 12 from the internal surgical site.

Referring now to FIGS. 1-3, the use and operation of forceps 10 will be briefly described. As will become apparent in view of the following, the specific features of proximal and distal segments 200, 300, respectively, of shaft 12 facilitate the use and operation of forceps 10. As shown in FIG. 1, jaw members 110, 120 of end effector assembly 100 are initially disposed in the spaced-apart position. In this position, as mentioned above, moveable handle 40 is disposed in the initial, spaced-apart position relative to fixed handle 50.

In use, end effector assembly 100 is maneuvered into position, e.g., inserted into the internal surgical site, such that tissue to be grasped, sealed, and/or divided, is disposed between jaw members 110, 120. Wheel 72 of rotation assembly 70 may be rotated to rotate shaft 12 about longitudinal axis "X-X" to thereby rotate end effector assembly 100 about longitudinal axis "X-X" to better position jaw members 110, 120 such that tissue is disposed therebetween. As mentioned above, although shaft 12 is permitted to rotate to position end effector assembly 100 as desired, shaft 12 is retained in fixed longitudinal position relative to housing 20 via the engagement of tabs 210 of proximal segment 200 of shaft 12 between retaining discs 23, 24 of distal cone 22 of housing 20.

Next, moveable handle 40 is pulled proximally relative to fixed handle 50 such that jaw member 110 is pivoted relative to jaw member 120 from the spaced-apart position to the approximated position to grasp tissue therebetween. More specifically, as moveable handle 40 is pulled proximally, the drive bar (not shown) is translated through shaft 12 and relative to end effector assembly 100 to translate drive pin 326 through cam slots 324 of mounting flanges 320 and through the cam slot (not shown) defined within jaw member 110 to urge jaw member 110 to rotate about pivot 103 from the spaced-apart position to the approximated position. Thereafter, electrosurgical energy may be supplied, e.g., via activation of switch 90 (FIG. 1), to tissue-sealing plate 112 and/or tissue-sealing plate 122 and conducted through tissue to effect a tissue seal, or otherwise treat tissue. As mentioned above, a knife blade (not shown) may then be advanced between jaw members 110, 120, e.g., via activation of trigger 82 of trigger assembly 80, to cut the previously treated tissue grasped between jaw members 110, 120 (or to cut untreated tissue, depending on a particular purpose). Finally, moveable handle 40 may be returned to the initial position, translating the drive bar (not shown) back through shaft 12 and relative to end effector assembly 100 such that jaw member 110 is urged to pivot back to the spaced-apart position.

With reference now to FIGS. 1-4B, the manufacture of shaft 12 for use with forceps 10 is described, keeping in mind that shaft 12 may similarly be manufactured to incorporate other features for use with other surgical instruments. Initially, each of the components of shaft 12, i.e., proximal segment 200, distal segment 300, and intermediate segment 400, are independently formed. More specifically, as mentioned above, proximal and distal segments 200, 300, respectively, may be formed via stamping to include the specific features thereof for coupling to housing 20 and end effector assembly 100, respectively. Intermediate segment 400, on the other hand, may be formed from tube-drawing and may then be cut to a desired length.

Once the proximal, distal, and intermediate segments 200, 300, 400, respectively, have been individually formed, they may be assembled together to form shaft 12. More specifically, proximal and distal segments 200, 300, respectively, are welded, e.g., laser-welded or spin-welded (i.e., friction-welded), to the respective proximal and distal ends 402, 404 of intermediate segment 400. Laser-welding involves applying a continuous or pulsed laser beam to the abutting ends of the segments to be joined, e.g., the distal end of proximal segment 200 and proximal end 420 of intermediate segment 400, or the proximal end of distal segment 300 and distal end 404 of intermediate segment 400, to heat and weld the segments to one another. Further, where precise alignment of the proximal and distal segments 200, 300, respectively, and/or the components thereof, e.g., tabs 210, cam slots 324, clevis 310, is required, the proximal and distal segments 200, 300, respectively, may be retained in fixed orientation relative to intermediate segment 400, e.g., in a suitable holder (not shown), during welding.

Spin-welding, or friction-welding involves positioning the segments to be welded to one another in abutting relation relative to one another, e.g., positioning proximal segment 200 in abutting relation with proximal end 402 of intermediate segment 400 and/or positioning distal segment 300 in abutting relation with distal end 404 of intermediate segment 400, and rotating one or both of the segments relative to the other at a high rate of speed to generate friction therebetween. The segment(s) are rotated relative to one another at a sufficiently high speed such that the friction generated therebetween heats the abutting ends of the segments to the welding point, or welding temperature, i.e., such that the abutting ends of the segments are heated to a molten or semi-molten state. Once this welding point has been reached, the segments are urged toward one another and the rotating segment(s) is rapidly decelerated until the rotation is fully stopped. With the abutting ends of the segments no longer rotating relative to one another to create friction therebetween, the welded joint formed upon urging of the molten or semi-molten ends of the segments to one another, e.g., welded joint 403 formed between proximal segment 200 and proximal end 402 of intermediate segment 400 or welded joint 405 formed between distal segment 300 and distal end 404 of intermediate segment 400, is permitted to cool and solidify, thereby fixedly joining the segments to one another.

Once the welded joints, e.g., welded joints 403, 405, have been formed and solidified, welded joints 403, 405 may be machined, or cut down such that welded joints 403, 405 are flush with the outer periphery of shaft 12. The inertia of the spinning forces during the spin-welding process inhibit welded joints 403, 405 from protruding inwardly into formed shaft 12 and, thus, the inner surface of welded joints 403, 405 need not be cut, or otherwise altered.

Proximal and distal segments 200, 300, respectively, of shaft 12 may be spin-welded to intermediate segment 400 of shaft 12 simultaneously with one another, or separately from one another, i.e., consecutively. To weld proximal and distal segments 200, 300, respectively, separately, for example, one of the segments, e.g., proximal segment 200, is rotated while intermediate segment 400 is held in fixed position to create weld joint 403 therebetween. Thereafter, the other segment, e.g., distal segment 300, is rotated relative to intermediate segment 400 and proximal segment 200 welded thereto, to create weld joint 405 therebetween, thus forming the completed shaft 12. When welding the other segment to intermediate segment 400 (after the initial segment has been welded to intermediate segment 400), the deceleration of the segment and the orientation of the segment once fully stopped may be controlled to facilitate precise alignment of proximal and distal segments 200, 300, respectively, relative to one another upon formation of shaft 12. In other words, the proximal and distal segments 200, 300, respectively, are clocked to one another to ensure proper alignment therebetween.

With regard to simultaneous spin-welding of shaft 12, intermediate segment 400 may be held stationary, while proximal and distal segments 200, 300, respectively, are rotated relative to intermediate segment 400 in abutting relation therewith at proximal and distal ends 402, 404, respectively, thereof. The rotating assemblies (not shown) configured to rotate proximal and distal segments 200, 300, respectively, relative to intermediate segment 400 during simultaneous spin-welding thereto may be mechanically and/or electrically coupled to one another to ensure adequate formation of both welded joints 403, 405 by ensuring that proximal and distal segments 200, 300, respectively, are rotated at substantially the same clock rate and that the spin-welding processes for welding proximal segment 200 to proximal end 402 of intermediate segment 400 and distal segment 300 to distal end 404 of intermediate segment are completed in substantially the same time. In addition, and if applicable to the particular shaft being assembled, ensuring that both the proximal and distal segments 200, 300, respectively, spin at the same clock rate and are decelerated and stopped in substantially the same time, i.e., ensuring that the proximal and distal segments 200, 300, respectively, are clocked to one another, allows precise alignment between the proximal and distal segments 200, 300, respectively, and the relative features associated with each segment, e.g., tabs 210, cam slots 324, clevis 310, etc.

In either welding process, the resulting shaft 12 includes proximal segment 200 welded to intermediate segment 400 at proximal end 402 thereof via first weld joint 403 and distal segment 300 welded to intermediate segment 400 at distal end 404 thereof via second weld join 405, thus forming a single, continuous shaft 12. Forming the three segments of shaft 12, e.g., proximal segment 200, distal segment 300 and intermediate segment 400, independently of one another and then joining the segments 200, 300, 400 to one another provides a simplified, customizable process for manufacturing shafts 12. More specifically, proximal and distal segments 200, 300, respectively, may be stamped (or otherwise formed) to include the required features for operably engaging shaft 12 to housing 20 and end effector assembly 100, respectively, (or, more generally, for engaging shaft 12 to any other components of the surgical instrument to be used in conjunction therewith) depending upon the specific configuration of housing 20 and end effector assembly 100, respectively. Intermediate segment 400, on the other hand, may be cut to a specific length as required for the particular surgical instrument to be used with shaft 12. Once the three segments 200, 300, 400 have been formed as desired, proximal segment 200 is welded (or otherwise formed) to proximal end 402 of intermediate segment 400 and distal segment 300 is welded (or otherwise formed) to distal end 404 of intermediate segment 400, ensuring that the specific components of proximal and distal segments 200, 300, respectively, are aligned with one another. In other words, the presently disclosed manufacturing process permits each of the segments 200, 300, 400 of shaft 12 to be independently formed and customized for a particular purpose, and then aligned later, e.g., during welding of the segments 200, 300, 400 to one another. As can be appreciated, this process obviates the need to rely on sophisticated stamping techniques for forming the entire shaft 12 as a single segment while also ensuring that the different features and/or components of the proximal and distal ends are properly aligned with one another during formation of shaft 12. Ultimately, shaft 12 may be secured within housing 20 at proximal end 16 thereof and may engage end effector assembly 100 thereon at distal end 14 thereof, for use in conjunction with forceps 10, as described above.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of manufacturing a shaft of a surgical instrument, comprising:
forming a proximal segment of the shaft to include at least one feature for operably engaging the shaft to a first component of the surgical instrument;
forming a distal segment of the shaft to include at least one feature for operably engaging the shaft to a second component of the surgical instrument;
forming an intermediate segment of the shaft;
welding the proximal segment of the shaft to a proximal end of the intermediate segment; and
welding the distal segment of the shaft to a distal end of the intermediate segment, wherein the welding of at least one of the proximal segment and the distal segment to the intermediate segment is configured such that the at least one feature of the proximal and distal segments are aligned in a pre-determined orientation relative to one another.

2. The method according to claim 1, wherein at least one of the proximal segment and the distal segment is welded to the intermediate segment via laser welding.

3. The method according to claim 1, wherein at least one of the proximal segment and the distal segment is welded to the intermediate segment via spin-welding.

4. The method according to claim 1, wherein the steps of welding the proximal segment of the shaft to a proximal end of the intermediate segment and welding the distal segment of the shaft to a distal end of the intermediate segment are performed simultaneously and are clocked to one another to ensure alignment of the proximal segment and the distal segment in the pre-determined orientation relative to one another.

5. The method according to claim 1, wherein the intermediate segment is formed via tube-drawing.

6. The method according to claim 1, wherein the formed intermediate segment is cut to a pre-determined length prior to welding of the proximal and distal segments thereto.

7. A method of manufacturing a shaft of a surgical instrument, comprising:
forming a proximal segment of the shaft;
forming a distal segment of the shaft;
forming an intermediate segment of the shaft;
spin-welding the proximal segment of the shaft to a proximal end of the intermediate segment and the distal segment of the shaft to a distal end of the intermediate segment, the proximal and distal segments clocked to one another during spin-welding to ensure alignment of the proximal and distal segments in a pre-determined orientation relative to one another.

8. The method according to claim 7, wherein at least one of the proximal segment and the distal segment are formed to include at least one feature for operably engaging the shaft to the surgical instrument.

9. The method according to claim 8, wherein the proximal segment of the shaft is formed to include at least one feature for operably engaging the shaft to a first component of the surgical instrument, and wherein the distal segment of the shaft is formed to include at least one feature for operably engaging the shaft to a second component of the surgical instrument.

10. The method according to claim 9, wherein the proximal and distal segments are clocked to one another during spin-welding to ensure proper alignment of the at least one feature of the proximal segment and the at least one feature of the distal segment in the pre-determined orientation relative to one another.

11. The method according to claim 7, wherein the proximal and distal segments are simultaneously spin-welded to the intermediate segment.

12. The method according to claim 7, wherein at least one of the proximal and distal segments is formed via stamping.

13. The method according to claim 7, wherein the intermediate segment is formed via tube-drawing.

14. The method according to claim 7, wherein the formed intermediate segment is cut to a pre-determined length prior to welding of the proximal and distal segments thereto.

15. A method of manufacturing a shaft of a surgical instrument, comprising:
stamping a proximal segment of the shaft to include at least one feature for operably engaging the shaft to a first component of the surgical instrument;
stamping a distal segment of the shaft to include at least one feature for operably engaging the shaft to a second component of the surgical instrument;
forming an intermediate segment of the shaft;
cutting the intermediate segment to a pre-determined length;
welding the proximal segment of the shaft to a proximal end of the intermediate segment; and
welding the distal segment of the shaft to a distal end of the intermediate segment.

16. The method according to claim 15, wherein at least one of the proximal segment and the distal segment is welded to the intermediate segment via laser welding.

17. The method according to claim 15, wherein at least one of the proximal segment and the distal segment is welded to the intermediate segment via spin-welding.

18. The method according to claim 15, wherein the welding of at least one of the proximal segment and the distal segment to the intermediate segment is configured such that the at least one feature of each of the proximal and distal segments are aligned in a pre-determined orientation relative to one another.

19. The method according to claim 15, wherein the intermediate segment is formed via tube-drawing.

* * * * *